(12) United States Patent
Rosenthal et al.

(10) Patent No.: US 6,285,903 B1
(45) Date of Patent: *Sep. 4, 2001

(54) INTRACORPOREAL DEVICE WITH RADIOPAQUE MARKER

(75) Inventors: Michael H. Rosenthal, Burlingame; Manuel A. Javier, Jr., Santa Clara; Sam G. Payne, Santa Clara; Stephen B. Pearce, Santa Clara; Randy J. Kesten, Mountain View, all of CA (US)

(73) Assignee: Eclipse Surgical Technologies, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/107,843

(22) Filed: Jun. 30, 1998

(51) Int. Cl.$^7$ .................................................. A61B 5/05
(52) U.S. Cl. ................................. 600/433; 600/424
(58) Field of Search ..................... 600/424, 426, 600/431, 433; 128/899; 604/280; 606/7, 10–19

(56) References Cited

U.S. PATENT DOCUMENTS

| | | | |
|---|---|---|---|
| 4,419,095 | 12/1983 | Nebergall et al. | 604/96 |
| 4,571,240 | 2/1986 | Samson et al. | 604/96 |
| 4,588,399 | 5/1986 | Nebergall et al. | 604/280 |
| 4,838,879 | 6/1989 | Tanabe et al. | 604/280 |
| 4,938,220 | 7/1990 | Mueller, Jr. | 128/658 |
| 4,994,071 | 2/1991 | MacGregor | 606/194 |
| 5,183,470 | 2/1993 | Wettermann | 604/281 |
| 5,203,777 | * 4/1993 | Lee | 604/280 |
| 5,429,617 | 7/1995 | Hammersmark et al. | 604/264 |
| 5,749,825 | * 5/1998 | Fischell et al. | 600/3 |
| 5,771,895 | * 6/1998 | Slager | 128/662.06 |
| 5,824,042 | * 2/2000 | Lombardi et al. | 623/1 |
| 5,885,272 | * 3/1999 | Aita et al. | 606/7 |
| 5,921,978 | * 7/1999 | Thompson et al. | 604/529 |
| 6,004,328 | * 12/1999 | Solar | 606/108 |
| 6,016,439 | * 1/2000 | Acker | 600/411 |
| 6,024,763 | * 2/2000 | Lenker et al. | 623/1 |
| 6,036,682 | * 3/2000 | Lange et al. | 604/529 |
| 6,063,111 | * 5/2000 | Hieshima et al. | 623/1 |

* cited by examiner

Primary Examiner—Marvin M. Lateef
Assistant Examiner—Eleni Mantis Mercader
(74) Attorney, Agent, or Firm—Edward J. Lynch; Ross M. Carothers; Ilene L. Janofsky

(57) ABSTRACT

An intracorporeal device generally having an elongate shaft with an asymmetric radiopaque marker disposed upon or within the distal end thereof. The radiopaque marker member enables the user to determine the orientation of the distal end of the device under fluoroscopic and similar imaging techniques. In certain embodiments the device is configured as a delivery catheter system having multiple delivery catheters, some or all of which may have radiopaque marker members disposed upon or within their distal ends. The delivery catheter system is configured in some embodiments to deliver an elongated diagnostic or therapeutic device to a desired location within a patient's heart.

33 Claims, 13 Drawing Sheets

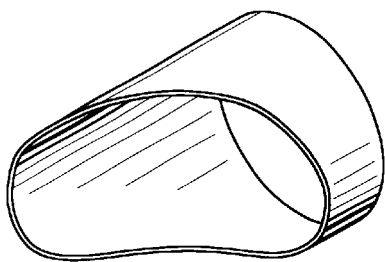
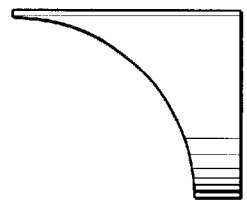
FIG. 7A                FIG. 7B
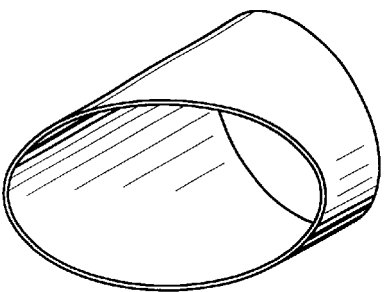
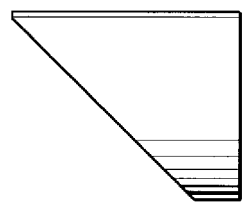
FIG. 8A                FIG. 8B
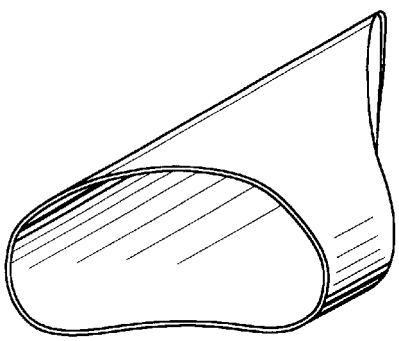
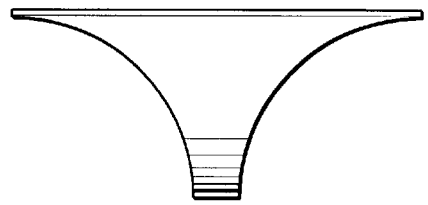
FIG. 9A                FIG. 9B

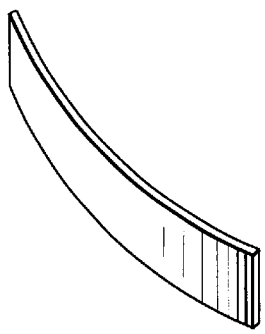
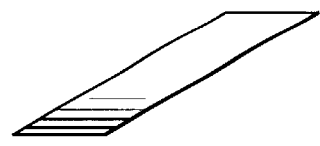
FIG. 10B
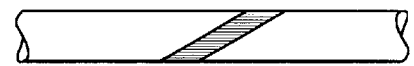
FIG. 10C
FIG. 10D
FIG. 10A
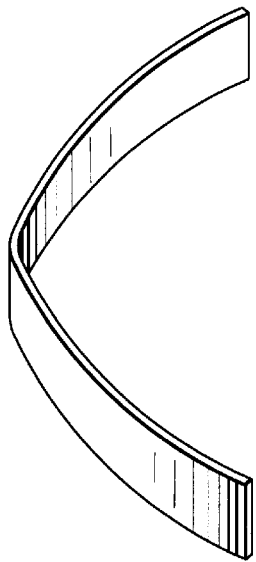
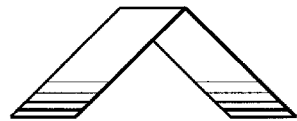
FIG. 11B
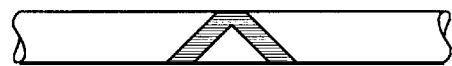
FIG. 11C
FIG. 11D
FIG. 11A

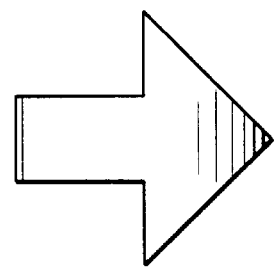
FIG. 14B
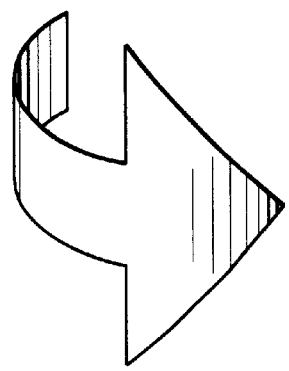
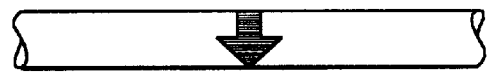
FIG. 14C
FIG. 14D
FIG. 14A
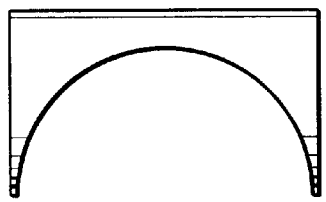
FIG. 15A
FIG. 15B
FIG. 15C

INTRACORPOREAL DEVICE WITH RADIOPAQUE MARKER

BACKGROUND OF THE INVENTION

This invention generally relates to devices and methods for visualization of elongated devices for therapeutic or diagnostic procedures in a patient's body. In particular, the invention relates to the positioning of the distal end of a catheter or catheter system within a patient's body using radiopaque marker members in conjunction with fluoroscopic or other suitable visualization systems. One specific application of the invention includes visualization of the distal end of an elongated delivery catheter while performing myocardial revascularization, tissue ablation, delivery of an angiogenic agent, or other desired therapy.

Myocardial revascularization typically involves tissue ablation, tissue injury, or formation of one or more channels in a patient's heart wall which defines the heart chamber, particularly the left ventricle. The first trials of the revascularization process were made by Mirhoseini et al. *Lasers in General Surgery* (Williams & Wilkins; 1989), pp. 216–223. Other early disclosures of this procedure are found in an article by Okada et al. in Kobe J. Med. Sci 32, 151–161, October 1986 and in U.S. Pat. No. 4,658,817 (Hardy). Both of these references describe intraoperative revascularization procedures which require the chest wall to be opened and which include formation of the revascularization channels completely through the heart wall, i.e., the epicardium, myocardium and endocardium.

Copending application Ser. No. 08/561,526 filed on Nov. 21, 1995 (Aita et al.), which is incorporated herein in its entirety, describes an intravascular system for myocardial revascularization which is introduced percutaneously into a peripheral artery and advanced through the patient's arterial system into the left ventricle of the patient's heart. The revascularization channels are not usually formed through the entire heart wall but only the endocardium and into the myocardium from within the left ventricle. This procedure eliminates the need of the prior intraoperative procedures to open the chest cavity and to penetrate through the entire heart wall in order to form the channel. While the percutaneous methods and systems for introducing revascularization devices developed by Aita et al. represent a substantial advance, one of the difficulties in revascularizing a patient's left ventricle by means of a percutaneously introduced revascularization system has been accurately visualizing the location of the distal tip of the tissue ablaton or injury device to a desired region of the patient's endocardium and maintaining the placement of the distal end of the device against a desired region of the ventricular wall at a proper angle, i.e., perpendicular or nearly perpendicular to the endocardium, while the heart is beating. The anatomy of human hearts and particularly the relationship of the ascending aorta and the left ventricle can vary considerably from patient to patient. The entry angle from the ascending aorta through the aortic valve into the left ventricle of a human heart does not facilitate the easy access to the free wall of the patient's heart which in substantial part defines the left ventricle.

Prior methods have involved the use of a delivery catheter made from polymeric tubing with a radiopaque material impregnated within the polymer wall, or a symmetric band of radiopaque metal attached to the distal end of the delivery catheter. However, with these devices and methods it can be difficult to determine the precise axial and rotational orientation of the distal end of the delivery catheter due to the symmetries of the marking system when viewed under two dimensional fluoroscopy. This can be cured in part by rotating the fluoroscopy unit to a second viewing angle and visualizing the distal end of the catheter from the second angle. The second viewing angle will sometimes provide enough information for the operating physician to determine the precise orientation of the distal end of the catheter, however, this process is cumbersome and time consuming. Another option is to use a bi-planar fluoroscopic unit to take views from two different perspectives, however, this process is also cumbersome, and the equipment required to do so is expensive.

What has been needed is an improved system and method for visualizing a delivery catheter or delivery catheter system during a percutaneous procedure. In particular, what has been needed is a system and method for fluoroscopic visualization of a catheter that facilitates visualization under two dimensional fluoroscopy without the need to view from more than one plane. The present invention satisfies these and other needs.

SUMMARY OF THE INVENTION

The present invention is directed to devices and methods that incorporate a radiopaque marker member into an intracorporeal device having an elongated shaft with a distal and a proximal end. The radiopaque marker member is disposed upon or within the elongated shaft proximal of the distal end thereof and has a first radiopaque section spaced longitudinally or transversely from a second radiopaque section disposed upon or within the elongated shaft. Such a configuration allows the operator of the intracorporeal catheter to ascertain the orientation of the catheter by fluoroscopic imaging. Another embodiment of the invention incorporates a radiopaque marker member with an intracorporeal device having an elongate shaft with a proximal and distal end and a curvature. The marker member is disposed upon or within the elongate shaft proximal of the distal end and has a curved shape which conforms generally to the curvature of the shaft. The marker member has a first longitudinal section that does not completely surround a circumference of the shaft and a second longitudinal section that does completely surround the circumference of the shaft so as to create a fluoroscopic projection which reveals the orientation of the shaft.

In one preferred embodiment of the present invention, a radiopaque marker member is used in conjunction with a catheter delivery system for percutaneously delivering an elongated therapeutic or diagnostic device into the interior of a patient's heart chamber. The system provides access to a wide region of the patient's endocardium defining at least in part the heart chamber. Such a system is described in detail in copending application Ser. No. 08/962,530 filed Oct. 31, 1997 (Kesten et al.) which is incorporated by reference herein in its entirety.

The catheter delivery system of one embodiment of the invention generally includes a first delivery catheter which has a relatively straight main shaft section and a shaped distal shaft section having a discharge axis selected so that is generally aligned with or parallel to a longitudinal axis of the patient's left ventricle. A second delivery catheter is slidably and rotatably disposed within an inner lumen of the first delivery catheter and provided with a shaped distal section configured to have a discharge axis which is normal or near normal to the patient's endocardial layer which defines in part the left ventricle. A radiopaque marker member may be disposed on or within a distal section of either or both of the delivery catheters.

In one presently preferred embodiment of the invention the first segment of the distal shaft section is at an angle of about 95° to about 160°, preferably about 100° to about 140° with respect to a proximally adjacent second segment of the distal shaft section and the proximally adjacent second segment is at an angle of about 95° to about 160°, preferably about 100° to about 135° with respect to either the proximally adjacent main shaft section or a third segment of the distal shaft section proximally adjacent to the second segment.

In those embodiments where there is a third segment of the distal section, it is at an angle of about angle of about 110° to about 170°, preferably about 120° to about 150° with respect to proximally adjacent main shaft section. The first and second segments should each be about 0.5 to about 5, preferably about 0.5 to about 4 cm in length, with the total length of the shaped distal section with two segments being about 2 to about 6 cm. If the distal section has a third segment, it should have a length of about 1 to about 5 cm, preferably about 2 to about 4 cm. The length of the shaped distal section with three segments should be about 3 to about 8 cm, preferably about 4 to about 7 cm.

In another presently preferred embodiment, the shaped distal section of the first delivery catheter has a single angled segment which provides a discharge axis approximating the longitudinal axis or long dimension of the heart chamber. In this embodiment the single angled segment of the distal shaft section has a length of about 2 to about 8 cm, preferably about 4 to about 6 cm and is at an angle of about 95° to about 160°, preferably about 100° to about 140° with respect to a proximally adjacent portion of the main shaft section.

The second delivery catheter preferably has a relatively straight main shaft section and a distal section which is at an angle of about 80° to about 140°, preferably about 90° to about 120° with respect to the main shaft section thereof. The second delivery catheter should be at least 10 cm longer, preferably about 15 to about 50 cm longer, than the first delivery catheter and is about 100 to about 150 cm, preferably about 110 to about 140 cm in length. The shaped distal section of the second delivery catheter should have a radius of curvature of about 2 to 30 mm, preferably about 4 to about 20 mm between the main shaft section and the exit or discharge axis through the port in the distal end of the shaped distal section. The length of the shaped distal section is about 0.5 to about 4 cm, preferably about 1 to about 3 cm.

A presently preferred elongated therapeutic or diagnostic device for use with the catheter delivery system is a device for revascularization of tissue within the wall of the patient's heart, particularly for ablation of an ischemic region thereof. The ablation device is adapted to emit ablation energy from its distal end which may be based on laser, radiofrequency, ultrasonic or other high energy emissions. The ablation device is slidably disposed within the inner lumen of the second delivery catheter and is long enough so that the distal operative end can extend out the port in the distal end of the second delivery catheter and contact the endocardium while the proximal end is operatively connected to a source of ablation energy such as laser, RF, ultrasound and the like. Preferably, the distal extremity of the ablation device which extends out the distal end of the delivery catheter has sufficient rigidity to be self-supporting within the environment of the heart chamber.

In a presently preferred embodiment of practicing the method of the invention, the first delivery catheter of the catheter delivery system is introduced into a peripheral artery, such as the femoral artery, and advanced through the patient's arterial system until the distal end of the first catheter is disposed within the patient's left ventricle. The position of the first delivery catheter is adjusted by the physician under fluoroscopic observation of the shaft and/or the radiopaque marker member disposed thereon until the distal tip is oriented generally along or parallel to the longitudinal axis of the left ventricle. The second delivery catheter is advanced through the previously introduced first delivery catheter which has a distal end appropriately positioned within the left ventricle. The second delivery catheter is positioned within the inner lumen of the first delivery catheter under fluoroscopic imaging until the shaped distal section of the second delivery catheter is within the left ventricle normal to the endocardium.

The orientation of the distal tip of the second delivery catheter is ascertained by the image produced by the radiopaque marker member on or within the distal tip thereof. In this manner the elongated therapeutic or diagnostic device slidably disposed within the inner lumen of the second delivery catheter is properly oriented with respect to the endocardial surface of the heart chamber. The perpendicular orientation helps to maintain the position of the distal end of the device, particularly a channel forming device, against the heart wall during multiple heart cycles. The use of dye injections through a port in the distal end of first and/or the second delivery catheter may be employed to further facilitate the location of the distal end of these catheters.

These and other advantages of the invention will become more apparent from the following detailed description of the invention, when taken in conjunction with the accompanying exemplary drawings.

BRIEF DESCRIPTION OF THE DRAWINGS

FIGS. 7A–7B show a perspective view of an embodiment of a radiopaque marker member.

FIGS. 8A–8B show a perspective view of an embodiment of a radiopaque marker member.

FIGS. 9A–9B show a perspective view of an embodiment of a radiopaque marker member.

FIGS. 10A–10B show a perspective view of an embodiment of a radiopaque marker member.

FIGS. 10C–10D depict radiographic projections of a catheter system incorporating the embodiment of the radiopaque marker of FIGS. 10A and 10B.

FIGS. 11A–11B show a perspective view of an embodiment of a radiopaque marker member.

FIGS. 11C–11D depict radiographic projections of a catheter system incorporating the embodiment of the radiopaque marker of FIGS. 11A and 11B.

FIGS. 14A–14B show a perspective view of an embodiment of a radiopaque marker member.

FIGS. 14C–14D depict radiographic projections of a catheter system incorporating the embodiment of the radiopaque marker of FIGS. 14A and 14B.

FIG. 15A show a perspective view of an embodiment of a radiopaque marker member.

FIGS. 15B–15C depict radiographic projections of a catheter system incorporating the embodiment of the radiopaque marker of FIG. 15A.

DETAILED DESCRIPTION OF THE INVENTION

Figure 1A:
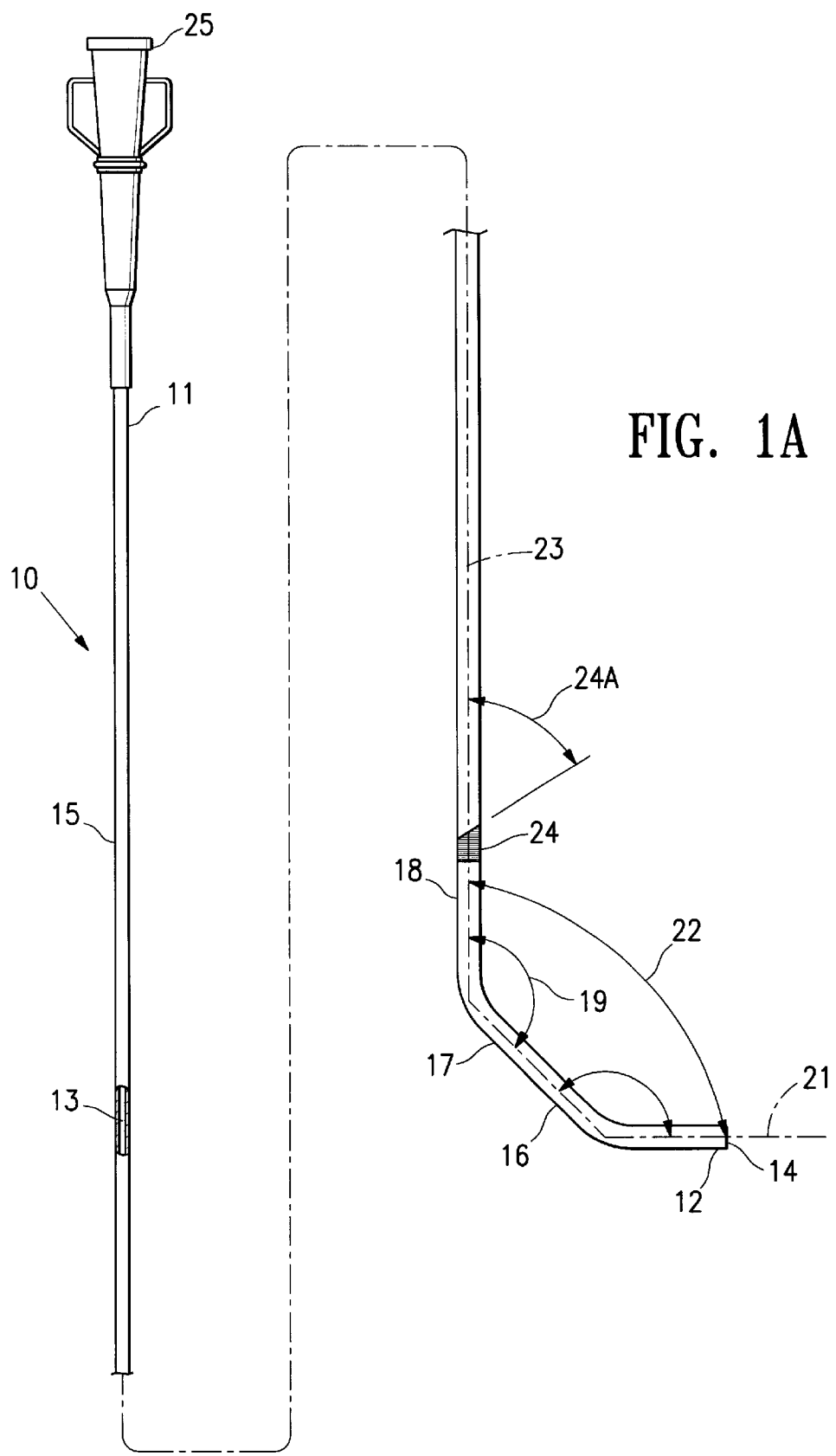
FIG. 1A shows an elevational view of an intracorporeal device or first delivery catheter.

FIG. 1A shows an embodiment of an intracorporeal device or first delivery catheter 10 which has features of the present invention. The first delivery catheter 10 has a proximal end 11, a distal end 12, an inner lumen 13 extending therein to and in fluid communication with a port 14 in the distal end, a relatively straight main shaft section 15 and a shaped distal section 16 having at least one segment 17 forming an angle 19 with respect to a proximally adjacent portion of the main shaft section 18. The shaped distal shaft section 16 has a discharge axis 21 which forms an angle 22 with respect to a longitudinal axis 23 of the main shaft section. Disposed upon the first delivery catheter 10 proximal to the distal end 12 is a radiopaque marker member 24. The embodiment of the radiopaque marker member 24 shown in FIG. 1A has a generally cylindrical wedge shaped configuration with a proximal end that forms an angle 24A with the longitudinal axis 23 of the main shaft section. Angle 24A can be from about 30° to about 80°, preferably about 45° to about 70° and more preferably about 55° to 65°. The radiopaque marker member 24 can be made from a radiopaque metal such as gold, platinum, tantalum or the like. It may also be made from a powdered radiopaque material that is mixed with a polymer that can be part of a catheter wall or mixed separately and bonded to the catheter wall. Suitable radiopaque materials can be tantalum powder, gold powder, bismuth, barium, and the like. The length of the radiopaque marker member can be from about 0.05 to about 0.5 inch, preferably about 0.1 to about 0.3 inch, more preferably about 0.2 to about 0.25 inch. The thickness of the radiopaque marker member can be from about 0.0001 to about 0.020 inch, preferably about 0.001 to about 0.003 inch, more preferably about 0.0015 to about 0.002 inch. The proximal end 11 of the first delivery catheter 10 is terminated with a standard female Luer connector 25 or the like.

The first delivery catheter 10 typically has a standard guiding catheter type construction consisting of one or more layers of polymer material that may optionally be reinforced with a high tensile coil or braid material to facilitate flexibility and torqueability. The layer of polymer material comprising the first delivery catheter may consist of a urethane, PVC, polyethylene, flouropolymer or other suitable biocompatible material. If the delivery catheter has multiple layers, those layers may be made from the same material or from various different materials such as those previously described. If a reinforcing coil or braid is included in the delivery catheter construction, it may be embedded within one or more layers or disposed between two different layers.

Figure 1B:
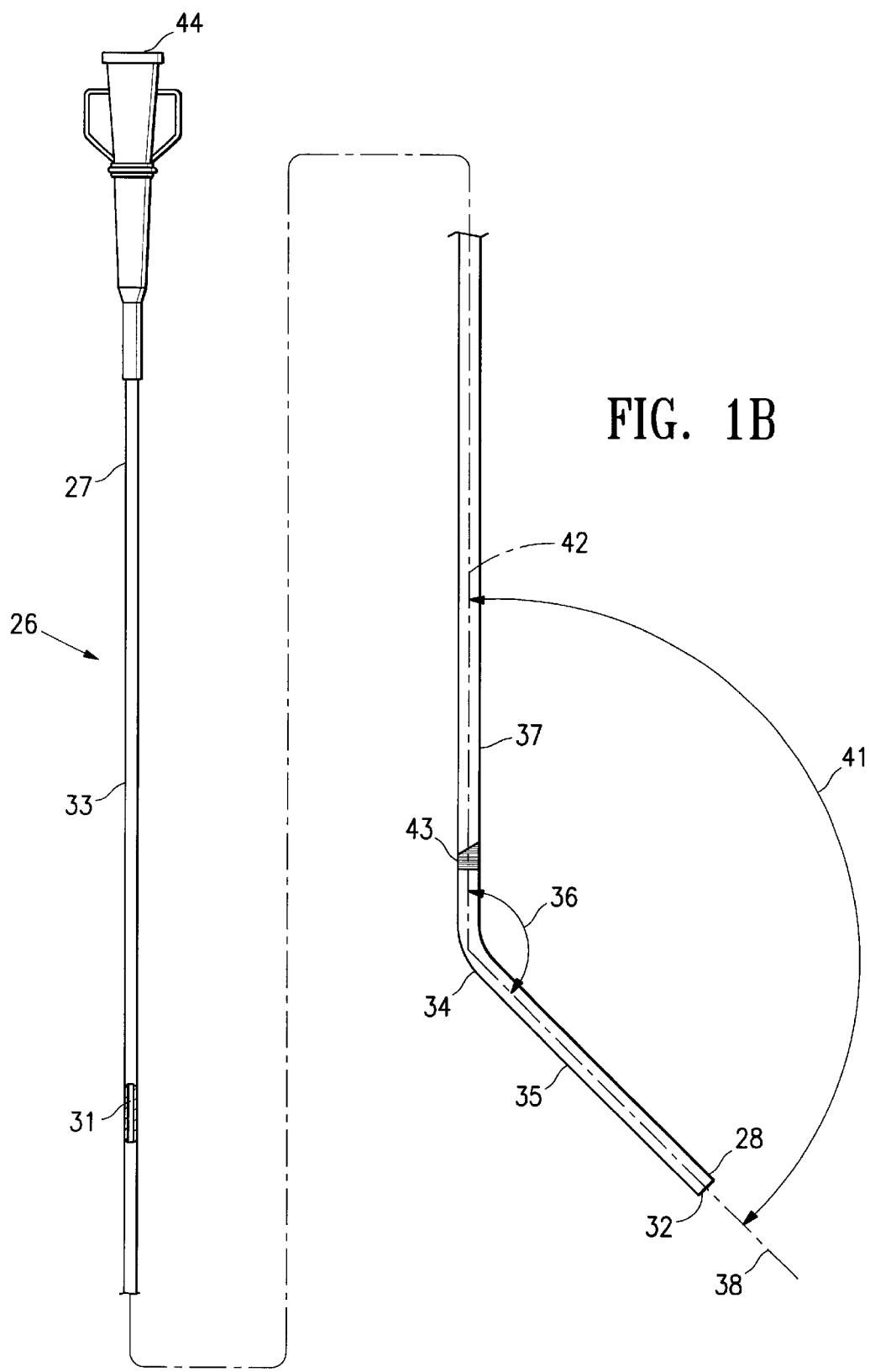
FIG. 1B shows an elevational view of an intracorporeal device or second delivery catheter.

FIG. 1B shows another embodiment of an intracorporeal device or second delivery catheter 26 which has features of the present invention. The construction of the second delivery catheter 26 can be similar to that of the first delivery catheter 10. The second delivery catheter 26 has a proximal end 27, a distal end 28, an inner lumen 31 extending therein to and in fluid communication with a port 32 in the distal end, a relatively straight main shaft section 33 and a shaped distal section 34 having at least one segment 35 forming an angle 36 with respect to a proximally adjacent portion 37 of the main shaft section 33. The shaped distal shaft section 34 has a discharge axis 38 which forms an angle 41 with respect to a longitudinal axis 42 of the main shaft section. Angle 41 can be from about 80° to about 140°, preferably about 90° to 120°. Disposed upon the second delivery catheter 26 proximal of the distal end 28 is a radiopaque marker member 43. The proximal end 27 of the second delivery catheter 26 is terminated with a standard female Luer connector 44 or the like.

Figure 1C:
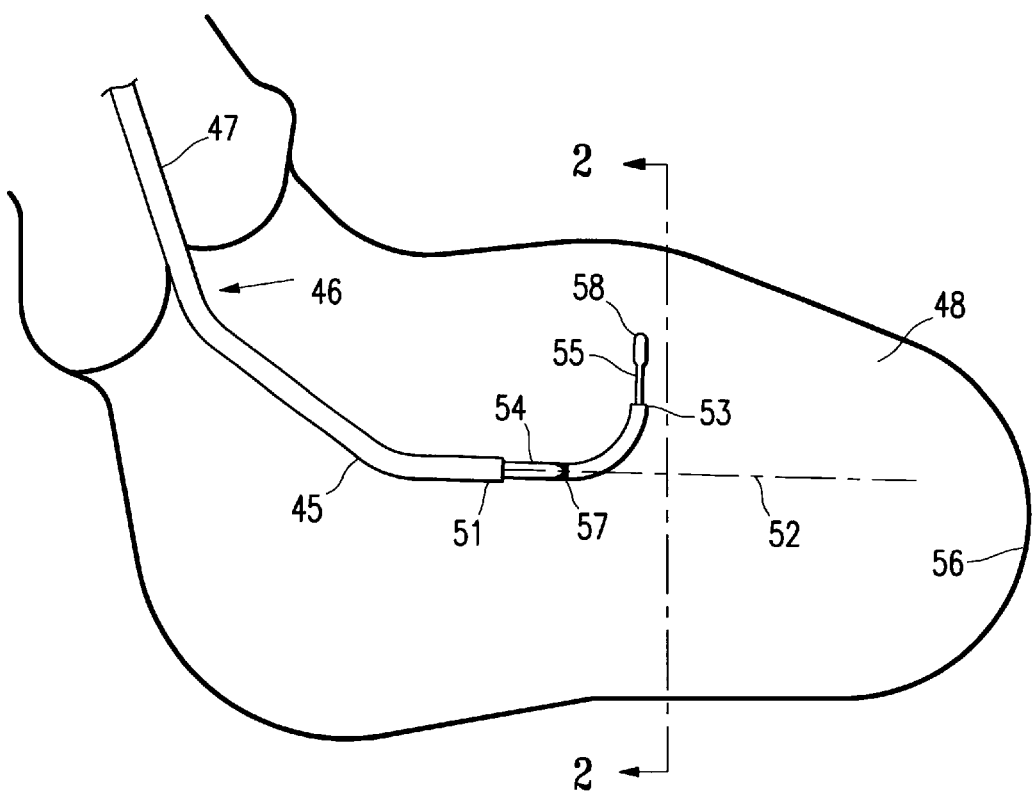
FIG. 1C shows an elevational view in partial section of a catheter delivery system which incorporates a radiopaque marker member disposed within a patient's left ventricle.

FIG. 1C shows an elevational view in partial section of a distal section 45 of a catheter delivery system 46 embodying characteristics of the present invention. A first delivery catheter 47 has been positioned within the left ventricle 48 such that a distal end 51 thereof is substantially aligned with a longitudinal axis of the left ventricle 52. Extending from the distal end 51 of the first delivery catheter 47 is the distal end 53 of a second delivery catheter 54 which is slidably and rotatably disposed within the first delivery catheter. Extending from the distal end 53 of the second delivery catheter 54 is a elongated therapeutic or diagnostic device 55 that, in a preferred embodiment, is for revascularization of a heart wall 56. Disposed upon the second delivery catheter 54 proximal of the distal end 53 thereof, is a radiopaque marker member 57 which indicates the orientation of the distal end 53 of the second delivery catheter by the radiographic projection produced therefrom. The preferred catheter system 46 depicted in FIG. 1 has the ability to access a large percentage of the heart wall 56 of the left ventricle 48 by virtue of translating and rotating the second delivery catheter 54 within the first delivery catheter 47 and extending a distal end 58 of the elongated therapeutic or diagnostic device 55 so as to contact the heart wall 56 at various locations.

Figure 2:
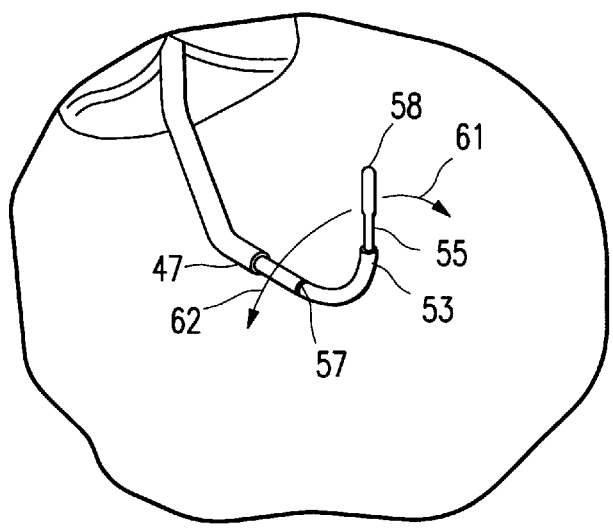
FIG. 2 shows a perspective view of a catheter delivery system which incorporates a radiopaque marker member disposed within a patient's left ventricle.

FIG. 2 depicts another view of the embodiment of the invention shown in FIG. 1 indicating by a first rotational arrow 61 and a second rotational arrow 62 a path the distal end 58 of the elongated therapeutic or diagnostic device 55 takes upon rotation of the distal end 53 of the second delivery catheter with respect to the distal end 47 of the first delivery catheter. FIG. 2 also indicates in a perspective view the change in appearance of the radiopaque marker member 57 in an orientation such as shown in FIG. 2 versus the orientation shown in FIG. 1.

Figure 3:
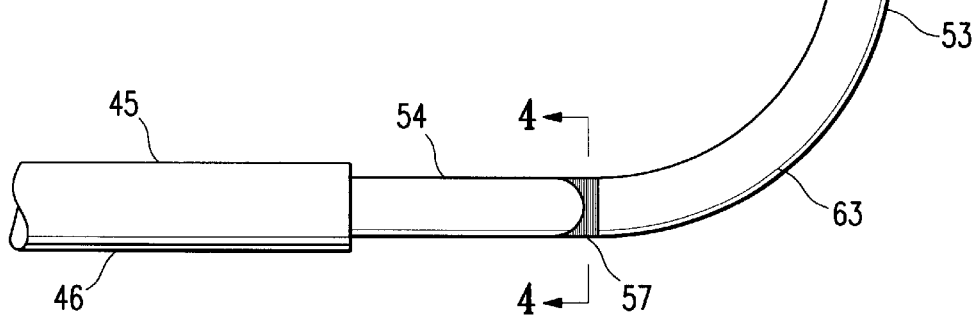
FIG. 3 shows an elevational view of the distal section of a catheter delivery system which incorporates a radiopaque marker member wherein the distal end of the second delivery catheter is pointing upwards.

FIG. 3 shows an enlarged view of the distal section 45 of the delivery catheter system 46 shown in FIG. 1 and FIG. 2. The radiopaque marker member 57 can also be seen in more detail in FIG. 3. The embodiment of the marker 57 shown in FIG. 3 consists of a generally wedge shaped cylindrical section of radiopaque material disposed over the second delivery catheter proximal of the distal end 53. An embodiment of the radiopaque marker member as shown in FIG. 3 can be made from a variety of materials, including, a radiopaque metal such as gold, tantalum, platinum, or the like. The marker 57 could also be made from a polymer material loaded with a radiopaque material, such as tantalum powder, bismuth, or the like. In addition, a radiopaque powder or material as indicated above could be embedded, extruded or molded into a second delivery catheter wall 63 in the shape of the radiopaque marker member 57.

Figure 4:
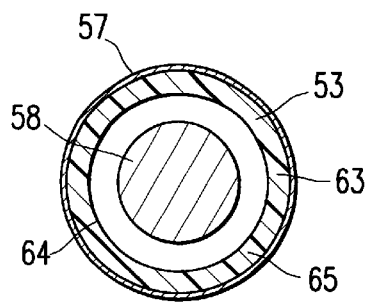
FIG. 4 depicts a cross sectional view of the catheter delivery system of FIG. 3 taken at section 4—4.

FIG. 4 shows a cross-sectional view of the distal end 53 of the second delivery catheter 54, the radiopaque marker member 57, and an elongated therapeutic or diagnostic device 58 taken at section 4—4 of FIG. 3. As indicated in FIG. 4, the radiopaque marker member 57 is preferably disposed around the outside of the distal end 53 of the second delivery catheter. The radiopaque marker member 57 could also be embedded within the wall 63 of the second delivery catheter, or be affixed to the inside wall surface 64 of the second delivery catheter. The radiopaque marker member 57 can be attached by means of an adhesive such as cyanoacrylate or other suitable adhesive or epoxy. In embodiments where the marker is embedded within the wall of the first delivery catheter 63, it is mechanically held in place by the surrounding wall material 65. A similar structure is used for the distal end 51 of the first delivery catheter 47.

Figure 5:
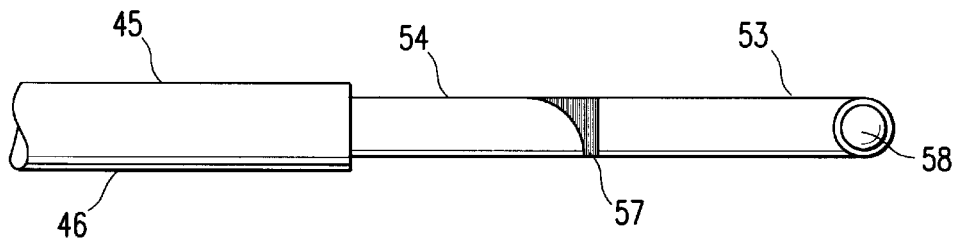
FIG. 5 shows an elevational view of the distal section of a catheter delivery system which incorporates a radiopaque marker member wherein the distal end of the second delivery catheter is pointing out of the page.

FIG. 5 shows the distal section 45 of the delivery catheter system wherein the distal end 53 of the second delivery catheter 54 is pointing out of the page such that the asymmetric nature of the radiopaque marker member 57 can be clearly seen. Although FIG. 5 does not show a radiographic representation of the distal section 45 of the catheter delivery system 46, such a radiographic projection of the marker 57 would look similar to the shape of the marker depicted. In this way, it is possible for the operator of the device or system 46 to determine the direction of the distal end 53 of the second delivery catheter by the projection of the radiopaque marker member 57 under fluoroscopic visualization.

Figure 6:
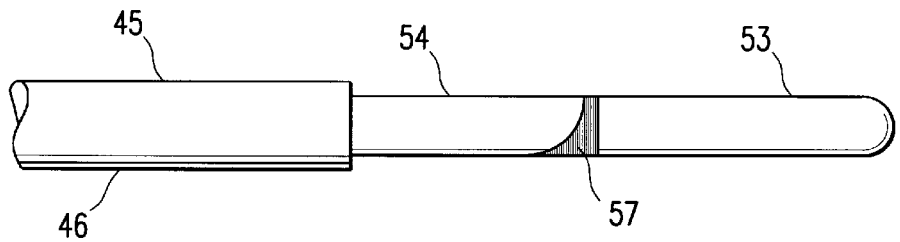
FIG. 6 shows an elevational view of the distal section of a catheter delivery system which incorporates a radiopaque marker member wherein the distal end of the second delivery catheter is pointing into the page.

FIG. 6 also shows the distal section 45 of the catheter delivery system 46 but with the distal end 53 of the second delivery catheter 54 facing into the page as indicated by the inverted shape of the radiopaque marker member 57 thereon. The elongated diagnostic or therapeutic device 55 shown in FIGS. 1–6 may be a device for the removal or injury of tissue for revascularization of heart tissue which emits laser energy, radio frequency energy, ultrasonic energy, mechanical ablation, or high pressure water jet ablation energy. The distal end 58 of the elongated therapeutic or diagnostic device may also be configured for delivery of therapeutic agents such as angiogenisis agents, such as VEGF, bFGF prostaglandin, nitric acid, viral vectors or the like. A configuration suitable for delivery for such agents preferably includes an elongated canula having a sharp at the distal end or some other similar configuration.

Figure 12A:
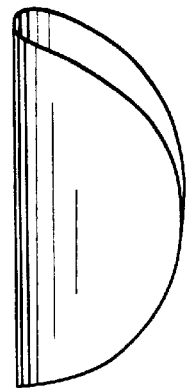
FIGS. 12A–12B show a perspective view of an embodiment of a radiopaque marker member.
Figure 12B:
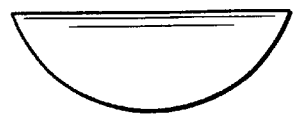
Figure 12C:
FIGS. 12C–12D depict radiographic projections of a catheter system incorporating the embodiment of the radiopaque marker of FIGS. 12A and 12B.
Figure 12D:
Figure 13A:
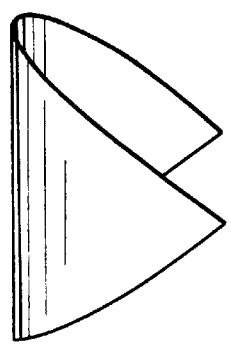
FIGS. 13A–13B show a perspective view of an embodiment of a radiopaque marker member.
Figure 13B:
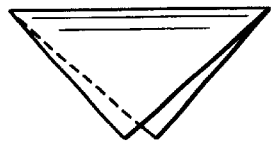
Figure 13C:
FIGS. 13C–13D depict radiographic projections of a catheter system incorporating the embodiment of the radiopaque marker of FIGS. 13A and 13B.
Figure 13D:
Figure 16A:
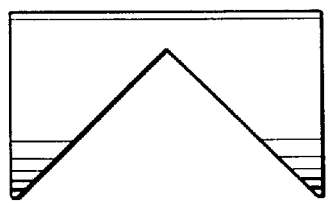
FIG. 16A show a perspective view of an embodiment of a radiopaque marker member.
Figure 16B:
FIGS. 16B–16C depict radiographic projections of a catheter system incorporating the embodiment of the radiopaque marker of FIG. 16A.
Figure 16C:
Figure 17A:
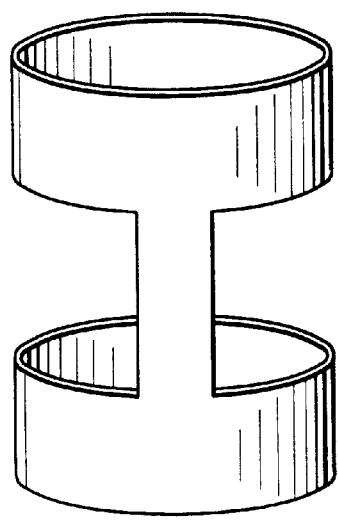
FIGS. 17A–17B show a perspective view of an embodiment of a radiopaque marker member.
Figure 17B:
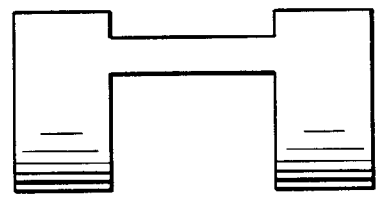
Figure 17C:
FIGS. 17C–17D depict radiographic projections of a catheter system incorporating the embodiment of the radiopaque marker of FIGS. 17A and 17B.
Figure 17D:
Figure 18A:
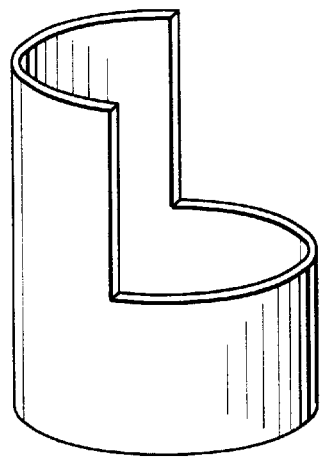
FIGS. 18A–18B show a perspective view of an embodiment of a radiopaque marker member.
Figure 18B:
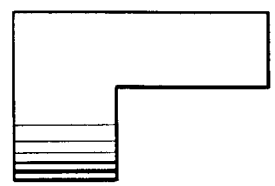
Figure 18C:
FIGS. 18C–18D depict radiographic projections of a catheter system incorporating the embodiment of the radiopaque marker of FIGS. 18A and 18B.
Figure 18D:
Figure 19A:
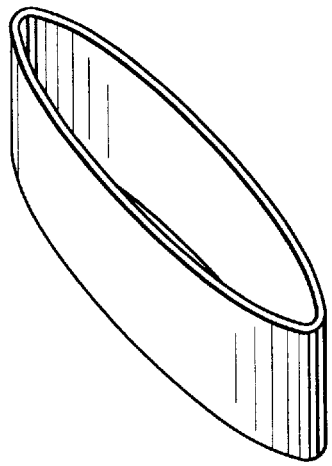
FIGS. 19A–19B show a perspective view of an embodiment of a radiopaque marker member.
Figure 19B:
Figure 19C:
FIGS. 19C–19D depict radiographic projections of a catheter system incorporating the embodiment of the radiopaque marker of FIGS. 19A and 19B.
Figure 19D:

FIGS. 7A–19D depict various shapes and configurations of various alternate embodiments of a radiopaque marker member that has characteristics of the invention. For each of the various embodiments shown in FIGS. 10A–19D, two radiographic projections that the marker would project are shown. Although the embodiments shown in FIGS. 7A–19D are depicted as free standing bodies of radiopaque material, similar radiographic results could be achieved by loading radiopaque powder or other suitable material on the surface of or integrally with the wall material of an elongated shaft in the shape of the marker embodiments shown. FIG. 12A depicts an embodiment of a radiopaque marker member which has features of the present invention and which can be formed from a radiopaque ribbon material. The marker member shown in FIG. 12A can be shaped to conform to the wall of a catheter having a radius of curvature which can be from about 0.005 to about 0.05 inch, preferably about 0.01 to about 0.040 inch, and more preferably about 0.025 to about 0.035 inch. The marker member can be shaped to conform and be bonded to the inside surface or the outside surface of a catheter wall. The marker member can also be shaped to conform to an interior portion of a catheter wall.

Numerous other embodiments of marker members having features of the invention can be similarly formed of ribbon material.

Figure 20A:
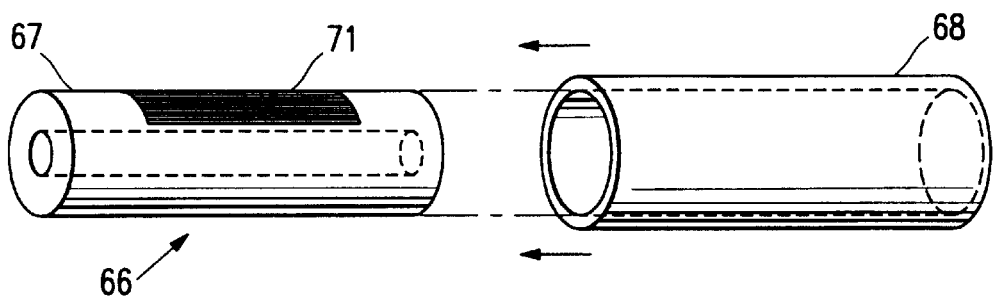
FIG. 20A shows an exploded view of a section of an elongate catheter shaft having a radiopaque marker member disposed between two concentric tubular members which comprise a shaft.
Figure 20B:
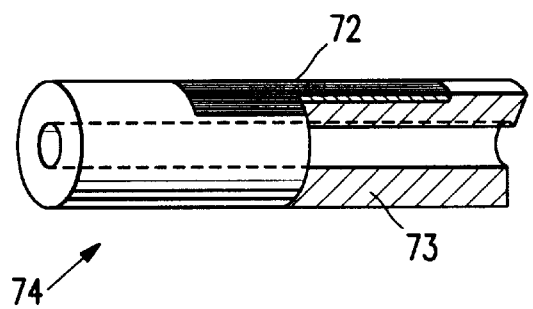
FIG. 20B shows a perspective view partially cutaway of a section of catheter shaft with a radiopaque marker member embedded in the shaft wall.

FIG. 20A illustrates a method of constructing a section of an elongate intracorporeal device 66 wherein the section has an elongated shaft formed of a first tubular member 67 disposed within a second tubular member 68 with a radiopaque marker member 71 disposed between said tubular members. FIG. 20B is a perspective view in partial cut-away illustrating a radiopaque marker member 72 embedded in the wall 73 of an elongate intracorporeal device 74.

Figure 20C:
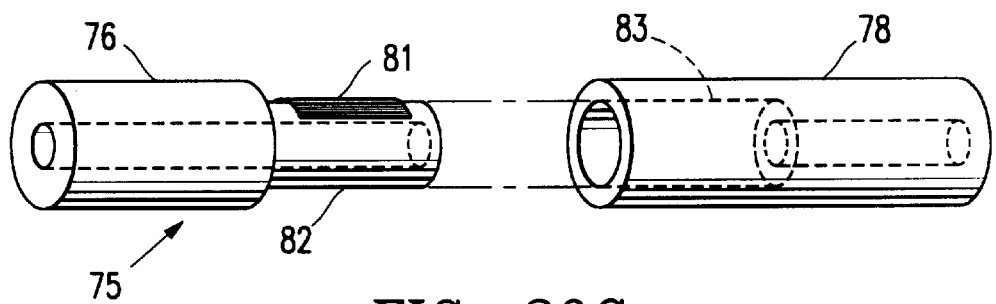
FIG. 20C shows an exploded view of a heat-fusion-bonded section of catheter shaft with a radiopaque marker member disposed between the mating surfaces of the fusion bond.

FIG. 20C illustrates an exploded view of a section of an elongate intracorporeal device 75 wherein a first portion 76 of the device is connected to a second portion 78 of the device by means of a step fusion process. A radiopaque marker member 81 is disposed between the first mating surface 82 of the first portion and the second mating surface 83 of the second portion 78 after the portions have been combined and fused.

Figure 21A:
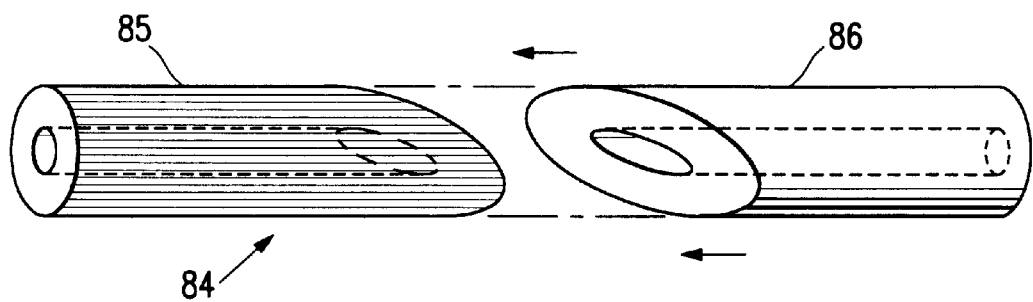
FIG. 21A shows an exploded view of a section of catheter shaft having a union between two separate portions of catheter shaft with one portion of catheter shaft being more radiopaque than the second portion.
Figure 21B:
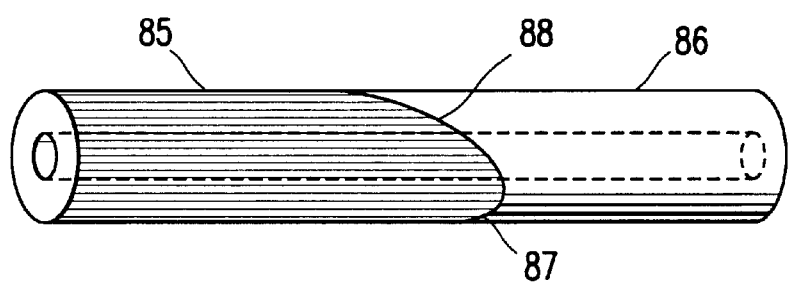
FIG. 21B shows a perspective view of the catheter shaft section of FIG. 21A.
Figure 21C:
FIGS. 21C–21D depict radiographic projections of a catheter system incorporating the embodiment of the radiopaque marker of FIGS. 21A and 21B.
Figure 21D:

FIG. 21A illustrates an exploded view of a section of an elongated intracorporeal device 84 where a first portion 85 of the device is connected to a second portion 86 in an asymmetric joint configuration. A radiopaque marker member results from the first portion 85 having a different radiopacity than the second portion 86 which creates an asymmetric radiopaque edge 88 at a boundary between the two portions as seen in FIG. 21B. FIGS. 21C and 21D depict approximate arbitrary radiographic projections of extremus orientations of the intracorporeal device section 84 shown in FIG. 21A.

Figure 22A:
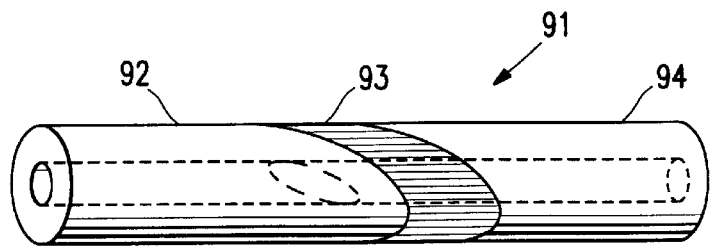
FIG. 22A shows a section of catheter shaft having a portion of the shaft which is more radiopaque than the remainder of the shaft.
Figure 22B:
FIGS. 22B–22C depict radiographic projections of the catheter shaft section of FIG. 22A.
Figure 22C:

FIGS. 22A–22C illustrate two variations of the embodiment of the radiopaque marker member 87 shown in FIG. 21B. FIG. 22A shows a section of an elongate intracorporeal device 91 wherein a first portion of the device 92 has been fused or bonded to a second portion 93 of the section which is then bonded or fused to a third portion 94 of the device. The second portion 93 has a different radiopacity than the first portion 92 or the third portion 94. FIG. 22B and FIG. 22C show approximate and arbitrary radiographic projections of the section of elongate intracorporeal device 91 of FIG. 22A.

Figure 23A:
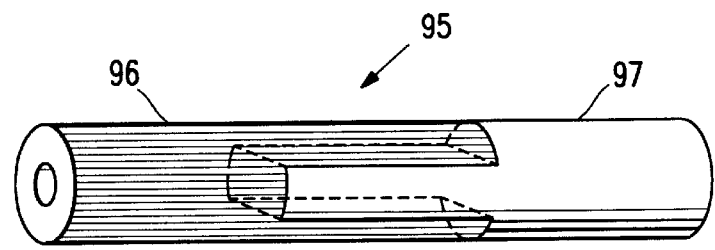
FIG. 23A shows a section of catheter shaft having a first portion of the shaft which is more radiopaque than a second portion with the portions joined so as to form a transition having a radiopaque edge.
Figure 23B:
FIGS. 23B–23C depict radiographic projections of the catheter shaft section of FIG. 23A.
Figure 23C:

FIG. 23A shows a section of elongate intracorporeal device 95 which has a first portion of the device 96 and a second portion of the device 97 wherein the first and second portions have different radiopacities. FIG. 23B and FIG. 23C show approximate and arbitrary radiographic projections of the section of elongate intracorporeal device 95 of FIG. 23A.

Although certain embodiments have been described with particularity, these are meant to illustrate the invention and are not limiting. More specifically, a number of variations in the geometry, construction, manufacture, and medical procedure use, are contemplated that will not depart from the spirit of this invention. Accordingly, reference should be made to the appended claims in order to ascertain the scope of this invention.

What is claimed is:

1. An intracorporeal device comprising:
   a) an elongated shaft having a proximal end and a shaped distal end defining a deflection plane; and
   b) an asymmetric radiopaque marker member disposed on the elongated shaft proximal to the shaped distal end thereof, the radiopaque marker having a first radiopaque section spaced longitudinally or transversely from a second radiopaque section and an asymmetrical plane which passes through a longitudinal axis of the elongated shaft and which is parallel to the deflection plane so as to allow an operator to fluoroscopically detect the orientation of the distal end of the elongated shaft within a patient.

2. The intracorporeal device of claim 1 wherein the radiopaque marker member is disposed within the elongated shaft.

3. The intracorporeal device of claim 1 wherein the radiopaque marker member is comprised of a radiopaque metal.

4. The intracorporeal device of claim 1 wherein the radiopaque marker member is comprised of a polymeric material loaded with a radiopaque material.

5. The intracorporeal device of claim 1 wherein the radiopaque marker member is formed by a boundary between a first cylindrical shaft portion and an adjacent second cylindrical shaft portion, wherein the first shaft portion has a different radiopacity than the second shaft portion.

6. The intracorporeal device of claim 1 wherein the radiopaque marker member is affixed to the inside wall surface of the shaft.

7. The intracorporeal device of claim 1 wherein the radiopaque marker member is an asymmetric joint connecting a first and second portion of the shaft.

8. An intracorporeal device comprising:
   a) an elongated shaft having a proximal end and a shaped distal end; and
   b) a radiopaque marker member disposed upon the elongated shaft proximal to the shaped distal end and having a shape conforming generally to the shape of the shaft, the marker member having a first longitudinal section that does not completely surround a circumference of the shaft, and a second longitudinal section that does completely surround the circumference of the shaft so as to create a radioscopic projection which reveals the orientation of the distal end of the elongated shaft.

9. The intracorporeal device of claim 8 wherein the radiopaque marker member is disposed within the elongated shaft.

10. The intracorporeal device of claim 8 wherein the radiopaque marker member is comprised of a radiopaque metal.

11. The intracorporeal device of claim 8 wherein the radiopaque marker member is comprised of a polymeric material loaded with a radiopaque material.

12. The intracorporeal device of claim 8 wherein the radiopaque marker member is formed by a boundary between a first shaft portion and a second shaft portion wherein the first shaft portion has a different radiopacity than the second shaft portion.

13. The intracorporeal device of claim 8 wherein the radiopaque marker member is affixed to the inside wall surface of the shaft.

14. The intracorporeal device of claim 8 wherein the radiopaque marker member is an asymmetric joint connecting a first and second portion of the shaft.

15. A delivery catheter system for the delivery of an elongated therapeutic or diagnostic device to perform a procedure in a region of a patient's heart wall which defines at least in part a left ventricle of the patient's heart, comprising:
   a) a first delivery catheter which has proximal and distal ends, a port in the distal end, an inner lumen extending therein to and in fluid communication with the port in the distal end, a relatively straight main shaft section and a shaped distal shaft section having at least one segment forming an angle with respect to a proximally adjacent portion of the main shaft section so that the shaped distal shaft section has a discharge axis which can generally be aligned with or parallel to a longitudinal axis of the patient's left ventricle; and b) a second elongated delivery catheter which is slidably and rotatably disposed within the inner lumen of the first delivery catheter, which is longer than the first delivery catheter and which has a proximal end and a shaped distal end, a port in the distal end, an inner lumen extending to and in fluid communication with the port in the distal end configured to slidably receive an elongated ablation device, an elongated main shaft section at least a portion of which is aligned with the discharge axis of the first delivery catheter and a distal section configured to have a discharge axis at an angle of about 80° to about 135° with respect to a portion of the main shaft section thereof aligned with the discharge axis of the first delivery catheter so as to be normal to the region of the heart wall to be subjected to the procedure; and c) a radiopaque marker member disposed on the elongated shaft of the second delivery catheter proximal to the shaped distal end thereof and which has a first radiopaque section spaced longitudinally or transversely from a second radiopaque section so as to allow an operator to fluoroscopically detect the orientation of the distal end of the elongated shaft within a patient.

16. The delivery catheter system of claim 15 wherein the shaped distal shaft section of the second delivery catheter is configured to have a discharge axis at an angle of about 90° to about 120° with respect to the portion of the main shaft section thereof aligned with the discharge axis of the first delivery catheter.

17. The delivery catheter system of claim 15 wherein the shaped distal section of the first delivery catheter has at least a first segment and a proximally adjacent second segment.

18. The delivery catheter system of claim 15 wherein the radiopaque marker member is disposed within the elongated shaft.

19. The delivery catheter system of claim 15 wherein the radiopaque marker member is comprised of a radiopaque metal.

20. The delivery catheter system of claim 15 wherein the radiopaque marker member is comprised of a polymeric material loaded with a radiopaque material.

21. The delivery catheter system of claim 15 wherein the radiopaque marker member is formed by a boundary between a first shaft portion and a second shaft portion wherein the first shaft portion has a greater radiopacity than the second shaft portion.

22. The delivery catheter system of claim 15 wherein the radiopaque marker member is formed by a boundary between a first cylindrical shaft portion and an adjacent second cylindrical shaft portion, wherein the first shaft portion has a greater radiopacity than the second shaft portion.

23. The delivery catheter system of claim 15 wherein the radiopaque marker member is affixed to the inside wall of the elongated shaft.

24. The delivery catheter system of claim 15 further comprising a second radiopaque marker member disposed on the straight main shaft spaced proximally to the distal end thereof.

25. A delivery catheter system for the delivery of an elongated device to perform a therapeutic or diagnostic procedure in a region of a patient's heart wall which defines at least in part a left ventricle of the patient's heart, comprising a) a first delivery catheter which has proximal and distal ends, a port in the distal end, an inner lumen extending therein to and in fluid communication with the port in the distal end, a relatively straight main shaft section and a shaped distal shaft section having at least one segment forming an angle with respect to a proximally adjacent portion of the main shaft section so that the shaped distal shaft section has a discharge axis which can generally be aligned with or parallel to a longitudinal axis of the patient's left ventricle;

b) a second elongated delivery catheter which is slidably and rotatably disposed within the inner lumen of the first delivery catheter, which is longer than the first delivery catheter and which has a proximal end and a shaped distal end, a port in the distal end, an inner lumen extending to and in fluid communication with the port in the distal end configured to slidably receive and elongated ablation device, an elongated main shaft section at least a portion of which is aligned with the discharge axis of the first delivery catheter and a distal section configured to have a discharge axis at an angle of about 80° to about 135° with respect to a portion of the main shaft section thereof aligned with the discharge axis of the first delivery catheter so as to be normal to the region of the heart wall to be subjected to the procedure; and c) a radiopaque marker member disposed upon the elongated shaft of the second delivery catheter proximal to the shaped distal end and having a shape which conforms to the shape of the shaft and which has a first longitudinal section that does not completely surround a circumference of the shaft and a second longitudinal section that does completely surround the circumference of the shaft so as to create a radioscopic projection which reveals the orientation of the distal end of the elongated shaft.

26. The delivery catheter system of claim 25 wherein the shaped distal shaft section of the second delivery catheter is configured to have a discharge axis at an angle of about 90° to about 120° with respect to the portion of the main shaft section thereof aligned with the discharge axis of the first delivery catheter.

27. The delivery catheter system of claim 25 wherein the shaped distal section of the first delivery catheter has at least a first segment and a proximally adjacent second segment.

28. The delivery catheter system of claim 25 wherein the radiopaque marker member is disposed within the elongated shaft.

29. The delivery catheter system of claim 25 wherein the radiopaque marker member is comprised of a radiopaque metal.

30. The delivery catheter system of claim 25 wherein the radiopaque marker member is comprised of a polymeric material loaded with a radiopaque material.

31. The delivery catheter system of claim 25 wherein the radiopaque marker member is affixed to the inside wall of the elongated shaft.

32. The delivery catheter system of claim 25 further comprising a second radiopaque marker member disposed on the straight main shaft spaced proximally to the distal end thereof.

33. A delivery catheter system for the delivery of an elongated device to perform a therapeutic or diagnostic procedure in a region of a patient's heart wall which defines at least in part a left ventricle of the patient's heart, comprising a) a first delivery catheter which has proximal and distal ends, an inner lumen extending therein, a relatively straight main shaft section and a shaped distal shaft section having at least one segment forming an angle with respect to a proximally adjacent portion of the main shaft section so that the shaped distal shaft section has a discharge axis which can generally be aligned with or parallel to a longitudinal axis of the patient's left ventricle;

b) a second elongated delivery catheter which is slidably and rotatably disposed within the inner lumen of the first delivery catheter, which is longer than the first delivery catheter and which has a proximal end and a shaped distal end, an inner lumen configured to slidably receive an elongated ablation device, an elongated main shaft section at least a portion of which is aligned with the discharge axis of the first delivery catheter and the shaped distal section configured to have a discharge axis at an angle of about 80° to about 135° with respect to a portion of the main shaft section thereof aligned with the discharge axis of the first delivery catheter so as to be normal to the region of the heart wall to be subjected to the procedure; and c) a radiopaque marker member disposed within the elongated shaft of the second delivery catheter proximal to the shaped distal end so as to allow an operator to fluoroscopically detect the orientation of the distal end of the delivery catheter system within a patient.

* * * * *